(12) United States Patent
Yasunaga et al.

(10) Patent No.: US 9,671,376 B2
(45) Date of Patent: Jun. 6, 2017

(54) FLOW PATH SWITCHING VALVE

(71) Applicant: SHIMADZU CORPORATION, Kyoto (JP)

(72) Inventors: Kenichi Yasunaga, Kyoto (JP); Yoshiaki Maeda, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/367,147

(22) PCT Filed: Dec. 21, 2012

(86) PCT No.: PCT/JP2012/083349
§ 371 (c)(1),
(2) Date: Jun. 19, 2014

(87) PCT Pub. No.: WO2013/099823
PCT Pub. Date: Jul. 4, 2013

(65) Prior Publication Data
US 2014/0352827 A1 Dec. 4, 2014

(30) Foreign Application Priority Data
Dec. 26, 2011 (JP) ................................. 2011-283271

(51) Int. Cl.
F16K 11/00 (2006.01)
G01N 30/38 (2006.01)
(Continued)

(52) U.S. Cl.
CPC .............. *G01N 30/38* (2013.01); *F16K 11/02* (2013.01); *F16K 27/045* (2013.01); *G01N 30/22* (2013.01);
(Continued)

(58) Field of Classification Search
CPC ..... Y10T 137/86501; Y10T 137/86863; F16K 11/074; F16K 11/0743; G01N 2030/202; G01N 30/38
(Continued)

(56) References Cited

U.S. PATENT DOCUMENTS 3,085,440 A * 4/1963 Guenther ............... F16K 11/022
137/625.42
3,111,849 A * 11/1963 Broerman ............... G01N 30/24
73/863.71
(Continued)

FOREIGN PATENT DOCUMENTS

CN 2535630 Y 2/2003
JP 1-307575 A 12/1989
(Continued)

OTHER PUBLICATIONS

Chinese Office Action dated Jan. 7, 2015, issued in corresponding CN Patent Application No. 201280062927.7 with English translation (10 pages).
(Continued)

Primary Examiner — Reinaldo Sanchez-Medina
(74) Attorney, Agent, or Firm — Westerman, Hattori, Daniels & Adrian, LLP

(57) ABSTRACT

A base and a stator forming a housing are joined by a stator position adjustment member. The adjustment member is a ring-shaped member having an inner diameter that is equal to the outer forms of the base and the stator, and threads opposite to each other are provided to an upper portion and a lower portion of the inner circumferential surface, along the circumferential direction. A thread for being screwed with the thread is provided, in the circumferential direction, to each of an upper portion of an outer circumferential surface of the base and a lower portion of an outer circumferential surface of an outer wall member of the stator. When (Continued)

the adjustment member is rotated, the base and the stator move in the direction of separating from each other or in the direction of coming close to each other.

6 Claims, 4 Drawing Sheets

(51) Int. Cl.
    *F16K 27/04*     (2006.01)
    *F16K 11/02*     (2006.01)
    *G01N 30/22*     (2006.01)
    *G01N 30/20*     (2006.01)

(52) U.S. Cl.
    CPC . *G01N 2030/202* (2013.01); *Y10T 137/86863* (2015.04)

(58) Field of Classification Search
    USPC .... 137/269, 315.09, 625.15, 625.19, 625.46, 137/627.5; 73/863.71, 863.72
    See application file for complete search history.

(56) References Cited

U.S. PATENT DOCUMENTS

| | | | | |
|---|---|---|---|---|
| 3,139,755 A * | 7/1964 | Reinecke | ............... | G01N 30/20 73/23.42 |
| 3,426,796 A * | 2/1969 | Vanderlaan | ............ | F02M 41/16 137/625.11 |
| 3,443,592 A * | 5/1969 | Felmlee | ............... | F16K 11/0743 137/625.11 |
| 3,687,163 A * | 8/1972 | Nickels | ................. | F16K 11/076 137/625.11 |
| 3,752,167 A * | 8/1973 | Makabe | ............. | F16K 11/0743 137/625.41 |
| 5,417,204 A * | 5/1995 | Moesle, Jr. | ............ | A62B 9/006 128/202.14 |
| 5,419,208 A * | 5/1995 | Schick | ................. | F16K 11/085 137/625.17 |
| 6,202,698 B1 * | 3/2001 | Stearns | ................... | F16K 11/22 137/595 |
| 2004/0042864 A1 * | 3/2004 | Jacobsson | ............... | B23Q 5/06 409/232 |
| 2006/0008366 A1 * | 1/2006 | Kingsford | ................ | F04B 9/02 417/417 |
| 2010/0269936 A1 | 10/2010 | Tomita | | |
| 2012/0118141 A1 * | 5/2012 | Maeda | ................. | F04B 53/164 92/168 |

FOREIGN PATENT DOCUMENTS

| | | |
|---|---|---|
| JP | 8-210526 A | 8/1996 |
| JP | 2004-052648 A | 2/2004 |

OTHER PUBLICATIONS

International Search Report dated Jan. 29, 2013 issued in corresponding application No. PCT/JP2012/083349.

Office Action dated Apr. 28, 2016, issued in counterpart Chinese Patent Application No. 201280062927.7, with English translation. (11 pages).

Decision of Rejection dated Nov. 8, 2016, issued in counterpart Chinese Patent Application No. 201280062927.7, with English translation. (9 pages).

* cited by examiner

FLOW PATH SWITCHING VALVE

TECHNICAL FIELD

The present invention relates to a flow path switching valve used in an analytical device such as a liquid chromatograph, and more particularly, to a rotary switching valve including a stator having a plurality of ports for connecting flow paths, and a rotor having a surface that comes into close contact with the stator and a switching groove, on the surface, for communicating the ports of the stator, the switching valve being for switching connection of the ports by rotating the rotor.

BACKGROUND ART

With a high-speed liquid chromatograph, for example, it is necessary to switch between flow paths to be connected under the condition of high-pressure delivery of a mobile phase. As a flow path switching valve used under such condition of high pressure, a rotary switching valve including a stator having a plurality of ports for connecting flow paths, and a rotor having a surface that comes into close contact with the stator and a switching groove, on the surface, for communicating two ports of the stator (see Patent Document 1) may be used. The rotary switching valve switches the flow paths to be connected, by switching the ports to be communicated by rotating the rotor while keeping the flat surfaces of the stator and the rotor in close contact with each other.

An example of the structure of the rotary switching valve is shown in FIG. 4.

This switching valve has a cylindrical base 42 forming a lower portion of a housing and a stator 40 forming an upper portion of the housing fixed to each other by a plurality of screws 44. A plurality of ports 46 for connecting flow paths are provided at an upper surface of the stator 40. Each port 46 is open to a lower surface 41 of the stator 40 which is an upper flat surface inside the housing. A rotor 10 is accommodated inside the base 42. A switching groove 14 for communicating the plurality of ports 46 of the stator 40 is provided on the flat surface of the rotor 10, on the side of the stator 40. The flat surface of the rotor 10, on the side of the stator 40, is in close contact with the lower surface 41 of the stator 40.

The rotor 10 is held by a rotor holding unit 8, and the rotor holding unit 8 is provided at a tip end of a shaft 12. The shaft 12 is extended outside through a hole at a center portion of the base 42. A rotating mechanism (not shown) for rotating the shaft 12 is provided outside the base 42. The rotor holding unit 8 is rotated by the rotation of the shaft 12, and the rotor 10 is then rotated. When the rotor 10 is rotated, the position of the switching groove 14 changes, and the ports 46 of the stator 40 to be connected are switched.

A ring bearing 20 for suppressing movement of the shaft 12 is arranged at a lower portion inside the base 42. A bearing 22 for suppressing shaky rotation of the rotor holding unit 8 is inserted between an outer circumferential surface of the rotor holding unit 8 and an inner circumferential surface of the base 42. A spring 18 is inserted between the rotor holding unit 8 and the bearing 20 in a compressed manner. The rotor holding unit 8 is biased toward the stator 40 by the elastic force of the spring 18, and the rotor 10 is thereby pressed against the lower surface of the stator 40. The liquid tightness between the rotor 10 and the stator 40 is thereby enhanced, and liquid leakage from the switching groove 14 of the rotor 10 is prevented.

PRIOR ART DOCUMENT

Patent Document

Patent Document 1: Japanese Patent Laid-open Publication No. 1-307575

SUMMARY OF THE INVENTION

Problems to be Solved by the Invention

As the material for a rotary switching valve, generally, a soft material such as resin is used for a rotor, and a material harder than that of the rotor, such as stainless steel, is used for a stator. As in the example of FIG. 4, the rotor is made to rotate while being pressed against the stator by the elastic force of a spring, and thus, when the flow path switching valve is used for a long period of time, the flat surface of the rotor which is in contact with the stator becomes worn. As a result, the flatness of the surface of the rotor that is in contact with the stator is lost, and problems such as an increase in the torque for rotating the rotor, liquid leakage from the switching groove of the rotor, or cross contamination caused by liquid remaining in the worn portion of the rotor may arise. Also, when the rotor is worn, scrapings of the rotor are produced, and the scrapings may flow through the switching groove together with liquid and be led to an analytical column connected at a later stage of the switching valve to thereby cause deterioration in the analytical column.

To prevent the rotor from being worn, ceramics, which is a hard material, is sometimes used for the rotor. In this case, scrapings due to wear of the rotor are not produced, but to improve the sealing performance to the stator, the surface roughness of the flat surfaces, of the stator and the rotor, that are in contact with each other has to be made small and the degree of flatness has to be high. However, when such flat surfaces are pressed against each other by a strong force, a mirror-surface adhesion phenomenon called "linking" occurs, and there is a problem that the smoothness of the rotation operation of the rotor is impaired.

The material of the rotor is therefore generally resin. The liquid tightness between the resin rotor and the stator may be enhanced by increasing the pressing force of the rotor against the stator, but if the rotor is pressed against the stator with a great force, the wear of the rotor at the time of rotation of the rotor becomes great, and there is a problem that the lifespan of the switching valve becomes short. When the switching valve is to be used under a condition of high delivery pressure, high liquid tightness between the rotor and the stator is necessary, and the rotor has to be strongly pressed against the stator. On the other hand, when high liquid tightness between the rotor and the stator is not necessary according to the intended use, such as where the delivery pressure is not high, the rotor does not have to be pressed against the stator with such a great force.

However, conventional rotary switching valves are, in many cases, not able to change the pressing force of the rotor against the stator. Also, the pressing force of the rotor against the stator may be made variable based on the adjustment of the degree of tightening of a screw provided at a portion lower than the base, but the degree of tightening of a screw cannot be adjusted in a state where the switching valve is installed in an analytical device, and burdensome work of removing the switching valve from the analytical device, for example, has to be performed to adjust the pressing force of the rotor against the stator.

Accordingly, the present invention aims to facilitate the adjustment of the pressing force of the rotor against the stator without the need to remove the switching valve from the analytical device.

Solutions to the Problems

A flow path switching valve according to the present invention includes a base forming a lower portion of a housing, the base having a thread provided at an upper portion of an outer circumferential surface and in a circumferential direction, a stator forming an upper portion of the housing, the stator including a plurality of ports for connecting flow paths at an upper surface, the ports being open to a surface that is an upper flat surface inside the housing, the stator being fixed so that the stator does not rotate on a same flat surface as the upper flat surface with respect to the base, a rotor, accommodated inside the housing, having a flat surface that is in contact with the upper flat surface inside the housing, the rotor being provided with a switching groove, at the flat surface, that is a flow path for communicating the plurality of ports of the stator, a rotor rotating mechanism for holding the rotor and rotating the rotor, an elastic member, inserted between the base and the rotor in a compressed manner, for biasing the rotor toward the upper flat surface inside the housing by an elastic force, and a stator position adjustment member that is a ring-shaped member provided with a thread, at a lower portion of an inner circumferential surface, that is to be screwed with the thread provided at the outer circumferential surface of the base, the stator position adjustment member being for joining the base and the stator by being attached to the outer circumferential surface of the base and for relatively raising or lowering the stator with respect to the base by rotation.

Effects of the Invention

According to the flow path switching valve of the present invention, a thread is provided, in a circumferential direction, at an upper portion of an outer circumferential surface of a base forming a lower portion of a housing, and a stator position adjustment member that is a ring-shaped member provided with a thread, at a lower portion of an inner circumferential surface, that is to be screwed with the thread provided at the outer circumferential surface of the base is provided. Because the stator position adjustment member is attached to the outer circumferential surface of the base while rotatably holding a stator at an upper portion and for relatively raising or lowering the stator with respect to the base by rotation, the height of the stator may be changed simply by rotating the stator position adjustment member attached to the outer circumferential surface of the base. Since the height of a rotor is also changed according to the change in the height of the stator, the stroke of an elastic member that is inserted between the base and the rotor is changed by the rotation of the stator position adjustment member, and the pressing force of the rotor against the upper flat surface inside the housing may be changed. Accordingly, the force of pressing the rotor against the stator may be easily adjusted simply by rotating the stator position adjustment member on the outer circumferential surface of the housing.

EMBODIMENTS OF THE INVENTION

As a preferred embodiment of the present invention, one may be exemplified that is provided with a thread, at a lower portion of an outer circumferential surface of a stator, which is reverse from a thread provided at an upper portion of an outer circumferential surface of a base, according to which a stator position adjustment member is provided with a thread, at an upper portion of an inner circumferential surface, that is to be screwed with the thread provided at the lower portion of the outer circumferential surface of the stator, the stator position adjustment member being attached to the outer circumferential surfaces of the base and the stator and separating or bringing close to each other the base and the stator by rotation.

Also, as another preferred embodiment, a mode may be cited according to which the stator position adjustment member includes a stator presser for pressing a part of an upper surface of the stator from above, the stator position adjustment member being for relatively raising or lowering, with respect to the base, the height of the stator that is pressed upward by a rotor, by relatively raising or lowering the stator presser with respect to the base by rotation. According to this embodiment, it is not necessary to provide two types of threads on the inner circumferential surface of the stator position adjustment member or to provide a thread on the outer circumferential surface of the stator, and thus, the structure is simplified. Also, screwing of threads at the time of attaching the stator position adjustment member to a housing is simplified.

Additionally, a part of the base and a part of the stator are preferably engaged with each other in the rotation direction of the stator position adjustment member, and relative rotation between the base and the stator is preferably prevented. Then, the stator does not have to be pressed so as to be prevented from rotating at the time of turning of the stator position adjustment member, and adjustment of the pressing force of the rotor against the stator may be easily performed.

Figure 1:
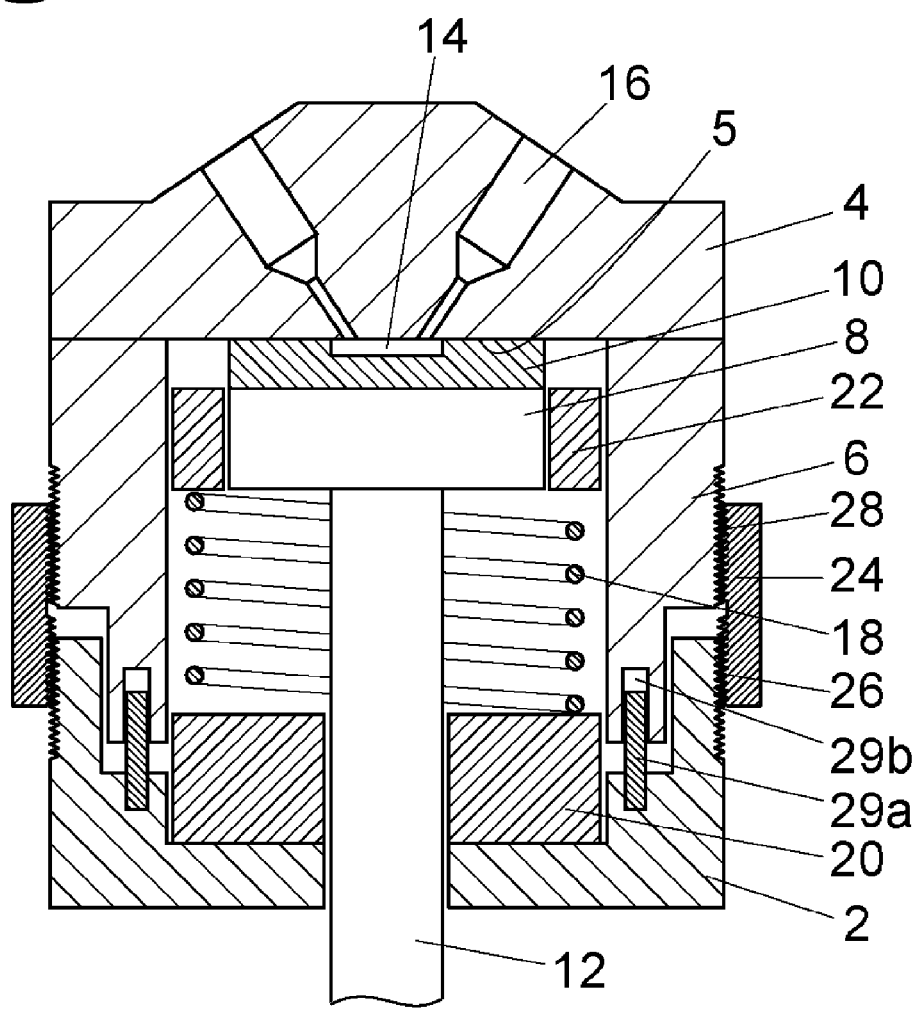
FIG. 1 is a cross-sectional diagram showing a structure of an embodiment of a flow path switching valve.

In the following, an embodiment of a flow path switching valve will be described with reference to the drawings. FIG. 1 is a cross-sectional diagram showing a structure of an embodiment of a rotary switching valve. The housing of this flow path switching valve is separated into an upper portion and a lower portion. The lower portion of the housing is formed by a base 2. The base 2 is to be fixed to an analytical device such as a liquid chromatograph, and forms a bottom portion and a lower portion of a side wall of the housing. The upper portion of the housing is formed by a stator 4. The stator 4 forms an upper lid portion of the housing, and also includes an outer wall member 6 forming an upper portion of the side wall. The base 2 and the stator 4 are joined by a stator position adjustment member 24 described below.

A plurality of ports 16 for connecting flow paths are provided at an upper surface of the stator 4. The ports 16 are extended to a lower surface 5, corresponding to an upper surface of an inner wall of the housing, of the stator 4. The lower surface 5 of the stator 4 is a flat surface.

A shaft 12 penetrates a center portion of the base 2. A rotor holding unit 8 is provided at a tip end of the shaft 12 inside the housing, and a rotor 10 is held by the rotor holding unit 8. At an upper surface of the rotor 10 facing the lower surface 5 of the stator 4, a switching groove 14 for communicating the ports 16 that are open to the lower surface 5 is provided.

A rotating mechanism (not shown) for rotating the shaft 12 is provided outside the base 2. The rotor holding unit 8 is rotated by the rotation of the shaft 12, and then the rotor 10 is rotated accordingly. The position of the switching groove 14 changes according to the rotation of the rotor 10, and the combination of the ports 16 to be communicated is switched.

A ring bearing 20 for suppressing movement of the shaft 12 is arranged at the lower portion of the base 2. A bearing 22 for suppressing shaky rotation of the rotor holding unit 8 is inserted between the outer circumferential surface of the rotor holding unit 8 and the inner circumferential surface of the outer wall member 6. A spring 18, as an elastic member, is inserted between the rotor holding unit 8 and the bearing 20 in a compressed manner. As the spring 18, a coil spring or a plate spring may be used. The rotor holding unit 8 is biased toward the stator 4 by the elastic force of the spring 18, and the rotor 10 is thereby pressed against the lower surface 5 of the stator 4. The liquid tightness between the upper surface of the rotor 10 and the lower surface 5 of the stator 4 is thereby enhanced, and liquid leakage from the switching groove 14 of the rotor 10 is prevented.

As described above, the base 2 and the stator 4 are joined by the stator position adjustment member 24. The stator position adjustment member 24 is a ring-shaped member having an inner diameter that is equal to the outer forms of the base 2 and the stator 4, and threads opposite to each other are provided to an upper portion and a lower portion of the inner circumferential surface, along the circumferential direction. A thread for being screwed with the thread on the inner circumferential surface of the stator position adjustment member 24 is provided, in the circumferential direction, to each of an upper portion 26 of the outer circumferential surface of the base 2 and a lower portion 28 of the outer circumferential surface of the outer wall member 6 of the stator 4.

When the stator position adjustment member 24 is rotated, the base 2 and the stator 4 move in the direction of separating from each other or in the direction of coming close to each other, by the action of the threads provided in the opposite directions. That is, when the stator position adjustment member 24 is rotated in one direction, the stator 4 moves in the direction of separating from the base 2, and when the stator position adjustment member 24 is rotated in the opposite direction, the stator 4 moves in the direction of coming close to the base 2.

Fitting portions (concavo-convex patterns) to be fitted with each other are formed to the opposing surfaces of the base 2 and the stator 4, and the center of rotation of the stator 4 is prevented from being shifted with respect to the base 2. Also, parallel pins 29a, as a mechanism for preventing relative rotation, and holes 29b into which the parallel pins 29a are to be inserted are provided to the opposing surfaces of the base 2 and the stator 4, and the base 2 and the stator 4 are allowed to move vertically, but not rotate, with respect to each other. Accordingly, the stator 4 is raised or lowered according to the rotation of the stator position adjustment member 24 without rotating. Additionally, any number of parallel pins 29a and holes 29b may be provided.

When the relative position of the stator 4 to the base 2 is changed, the stroke of the spring 18 that is inserted between the rotor holding unit 8 and the bearing 20 is changed, and the pressing force of the rotor 10 against the lower surface 5 of the stator 4 is changed. Accordingly, the pressing force of the rotor 10 against the lower surface 5 of the stator 4 may be easily changed by rotating the stator position adjustment member 24.

A mark may be given to the base 2 or the stator 4 to indicate the rotation position of the stator position adjustment member 24. This may facilitate the adjustment of the pressing force of the rotor 10 against the stator 4.

Figure 2:
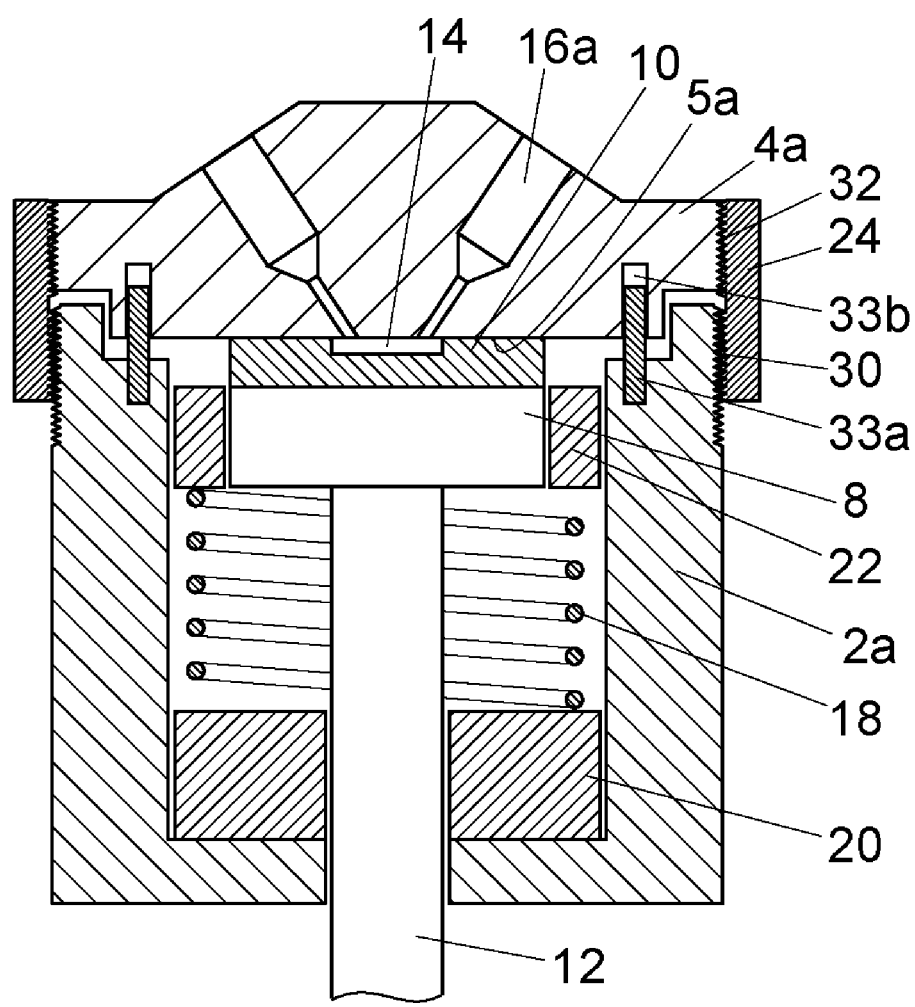
FIG. 2 is a cross-sectional diagram showing a structure of another embodiment of the flow path switching valve.

Additionally, changing the biasing force of the spring 18 on the rotor 10 in a state where the flow rate switching valve is attached to the device is easier as the position of the stator position adjustment member 24 is at a higher position of the housing. FIG. 2 is a cross-sectional diagram showing an embodiment where the stator position adjustment member 24 is arranged at a position higher than in the embodiment of FIG. 1.

In the embodiment of FIG. 2, a base 2a forms a bottom portion and a side wall portion of a housing. A stator 4a having ports 16a at an upper surface forms an upper lid portion of the housing. The base 2a and the stator 4a are joined by the same stator position adjustment member 24 as in the embodiment of FIG. 1. Threads for being screwed with threads formed on an inner circumferential surface of the stator position adjustment member 24 are formed, in a circumferential direction, to an upper portion 30 of an outer circumferential surface of the side wall portion of the base 2a and an outer circumferential surface 32 of the stator 4a. As in the embodiment of FIG. 1, fitting portions (concavo-convex patterns) to be fitted with each other are formed to the opposing surfaces of the base 2a and the stator 4a, and the center of rotation of the stator 4a is prevented from being shifted with respect to the base 2a. Also, parallel pins 33a and holes 33b into which the parallel pins 33a are to be inserted are provided to the opposing surfaces of the base 2a and the stator 4a, and the base 2a and the stator 4a are allowed to move vertically, but not rotate, with respect to each other. Accordingly, the stator 4 is raised or lowered according to the rotation of the stator position adjustment member 24 without rotating.

The stator 4a moves in the direction of separating from the base 2a or in the direction of coming close to the base 2a by the rotation of the stator position adjustment member 24. Since the stator position adjustment member 24 is arranged at the uppermost portion of the outer circumference of the housing, the pressing force of the rotor 10 against a lower surface 5a of the stator 4a may be easily changed by changing the stroke of the spring 18 that is inserted between the rotor holding unit 8 and the bearing 20 even in a state where the flow path switching valve is installed in the analytical device.

A mark may be given to the base 2a or the stator 4a to indicate the rotation position of the stator position adjustment member 24. This may facilitate the adjustment of the pressing force of the rotor 10 against the stator 4a.

Figure 3:
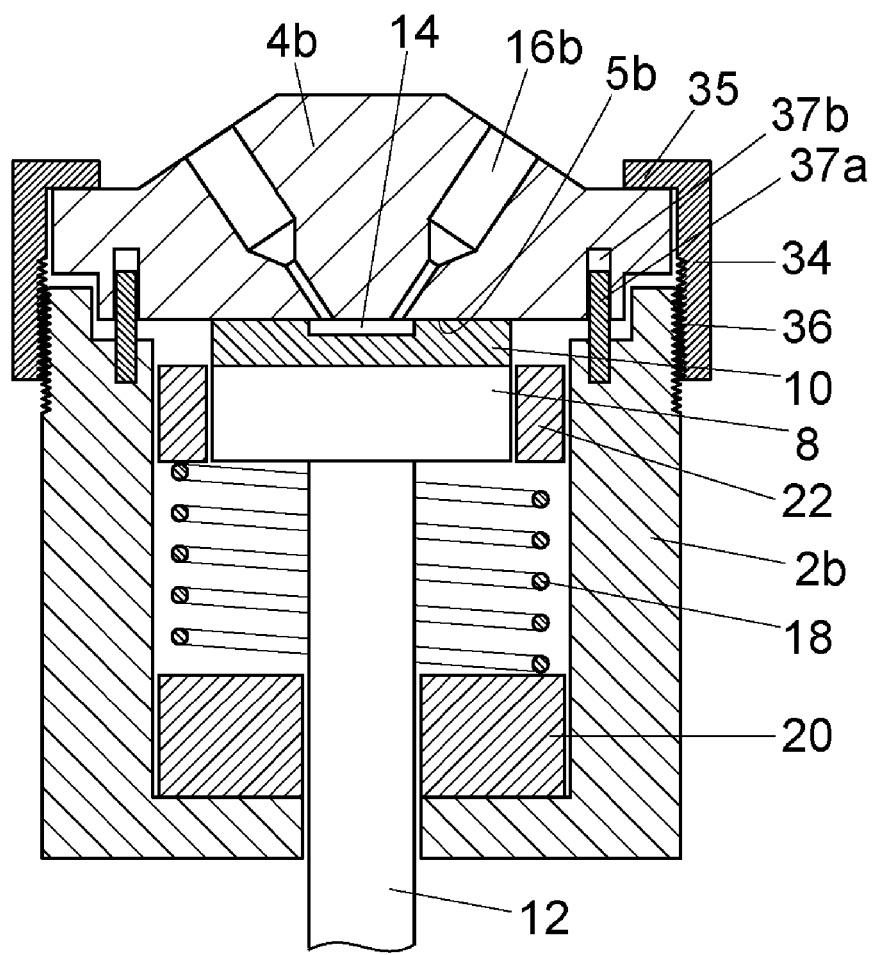
FIG. 3 is a cross-sectional diagram showing a structure of further another embodiment of the flow path switching valve.
Figure 4:
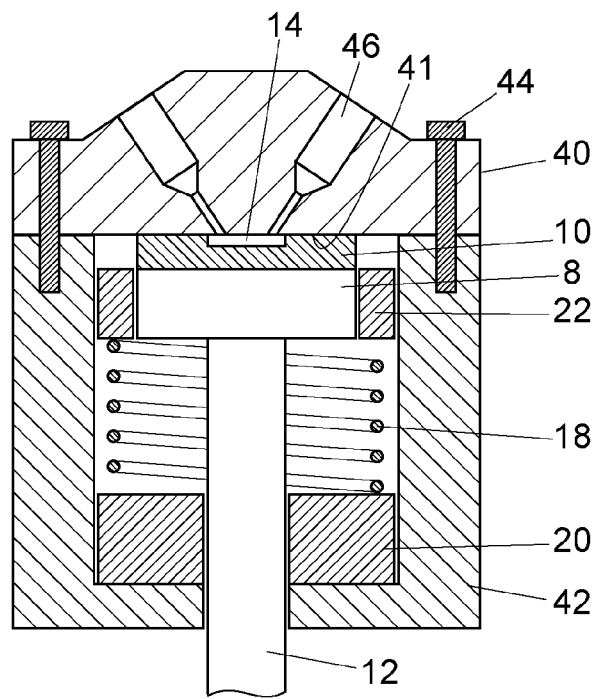
FIG. 4 is a cross-sectional diagram showing an example of a structure of a conventional flow path switching valve.

FIG. 3 is a cross-sectional diagram showing another embodiment of the flow path switching valve.

According to the flow path switching valve of this embodiment, a base 2b forms a bottom portion and a side wall portion of a housing, and a stator 4b having ports 16b at an upper surface forms an upper lid portion of the housing. The base 2b and the stator 4b are joined by a stator position adjustment member 34 different from the stator position adjustment member 24 of the embodiments of FIGS. 1 and 2. The stator position adjustment member 34 is a member whose cross section is L-shaped, and includes, at an upper end portion, a stator presser 35 for pressing a circumferential edge portion of the upper surface of the stator 4b. A thread is provided in the circumferential direction at a lower portion of the inner circumferential surface of the stator position adjustment member 34, and a thread for being screwed with the thread on the inner circumferential surface of the stator position adjustment member 34 is provided on an upper portion 36 of an outer circumferential surface of the base 2b, in the circumferential direction.

A thread is not provided to the outer circumferential surface of the stator 4b, and the stator 4b simply has the circumferential edge portion of its upper surface pressed by the stator presser 35 of the stator position adjustment member 34. The stator position adjustment member 34 is raised or lowered along the circumferential surface of the base 2b by rotating. The rotor 10 is pressed against a lower surface 5b of the stator 4b by the elastic force of the spring 18, and the stator 4b is thereby pressed upward at all times. Accordingly, when the stator position adjustment member 34 is raised or lowered by rotation, the stator 4b is raised or lowered accordingly.

Additionally, also in this embodiment, fitting portions (concavo-convex patterns) to be fitted with each other are formed to the opposing surfaces of the base 2b and the stator 4b, and the center of rotation of the stator 4b is prevented from being shifted with respect to the base 2b. Also, parallel pins 37a and holes 37b into which the parallel pins are to be inserted are provided to the opposing surfaces of the base 2b and the stator 4b, and the base 2b and the stator 4b are allowed to move vertically, but not rotate, with respect to each other. Accordingly, the stator 4 is raised or lowered according to the rotation of the stator position adjustment member 24 without rotating.

According to the embodiment described above, the pressing force of the rotor 10 against the stator 4b may be continuously changed by rotating the stator position adjustment member 34.

A mark may be given to the base 2b or the stator 4b to indicate the rotation position of the stator position adjustment member 34. This may facilitate the adjustment of the pressing force of the rotor 10 against the stator 4b.

Furthermore, the stator does not have to be a single component, and may be formed from a plurality of structural components.

DESCRIPTION OF REFERENCE SIGNS

2, 2a, 2b: Base
4, 4a, 4b: Stator
6: Outer wall member
8: Rotor holding unit
10: Rotor
12: Shaft
14: Switching groove
16, 16a, 16b: Port
18: Spring
20, 22: Bearing
24, 34: Stator position adjustment member
29a, 33a, 37a: Parallel pin

The invention claimed is:

1. A flow path switching valve comprising:
a base forming a lower portion of a housing, the base having a thread provided at an upper portion of an outer circumferential surface and in a circumferential direction;
a stator forming an upper portion of the housing, the stator including a plurality of ports for connecting flow paths at an upper surface, the ports being open to a surface that is an upper flat surface inside the housing;
a rotor, accommodated inside the housing, having a flat surface that is in contact with the upper flat surface inside the housing, the rotor being provided with a switching groove, at the flat surface, that is a flow path for communicating the plurality of ports of the stator;
a rotor rotating mechanism for holding the rotor and rotating the rotor;
an elastic member, inserted between the base and the rotor in a compressed manner, for biasing the rotor toward the upper flat surface inside the housing by an elastic force; and
a stator position adjustment member that is a ring-shaped member provided with a thread, at a lower portion of an inner circumferential surface, that is to be screwed with the thread provided at the outer circumferential surface of the base, the stator position adjustment member being for joining the base and the stator by being attached to the outer circumferential surface of the base, for adjusting pressure force of the rotor against the stator, and for relatively raising or lowering the stator with respect to the base by rotation.

2. The flow path switching valve according to claim 1, wherein a thread that is opposite to the thread provided at the upper portion of the outer circumferential surface of the base is provided to a lower portion of an outer circumferential surface of the stator, and
wherein the stator position adjustment member is provided with a thread, at an upper portion of an inner circumferential surface, that is to be screwed with the thread provided at the lower portion of the outer circumferential surface of the stator, the stator position adjustment member being attached to the outer circumferential surfaces of the base and the stator and separating or bringing close to each other the base and the stator by rotation.

3. The flow path switching valve according to claim 1, wherein the stator position adjustment member includes a stator presser for pressing a part of an upper surface of the stator from above, the stator position adjustment member being for relatively raising or lowering, with respect to the base, a height of the stator that is pressed upward by the rotor, by relatively raising or lowering the stator presser with respect to the base by rotation.

4. The flow path switching valve according to claim 1, wherein a part of the base and a part of the stator are engaged with each other in a rotation direction of the stator position adjustment member, and relative rotation between the base and the stator are prevented.

5. The flow path switching valve according to claim 2, wherein a part of the base and a part of the stator are engaged with each other in a rotation direction of the stator position adjustment member, and relative rotation between the base and the stator are prevented.

6. The flow path switching valve according to claim 3, wherein a part of the base and a part of the stator are engaged with each other in a rotation direction of the stator position adjustment member, and relative rotation between the base and the stator are prevented.

* * * * *